United States Patent [19]

Schmidthaler

[11] Patent Number: 4,578,822

[45] Date of Patent: Apr. 1, 1986

[54] VISOR

[75] Inventor: Johann Schmidthaler, Binderlandweg, Austria

[73] Assignee: Optyl Eyewear Fashion International Corporation, Norwood, N.J.

[21] Appl. No.: 468,287

[22] Filed: Feb. 22, 1983

[30] Foreign Application Priority Data

Sep. 8, 1982 [AT] Austria ................................ 23088

[51] Int. Cl.[4] ............................................. A61F 9/04
[52] U.S. Cl. ................................................ 2/12; 2/452
[58] Field of Search ................... 2/12, 10, 199, 185 R, 2/177, 191, 452, 171

[56] References Cited

U.S. PATENT DOCUMENTS

| 58,907 | 10/1866 | Spence | 2/12 |
| 1,803,338 | 5/1931 | Magee | 2/12 |
| 2,491,137 | 12/1949 | Sameth | 2/452 |
| 2,859,448 | 11/1958 | Gaichel | 2/12 X |
| 3,383,707 | 5/1968 | McNeill | 2/12 |
| 4,192,017 | 3/1980 | Fay | 2/12 |
| 4,193,133 | 3/1980 | Laibach et al. | 2/10 |
| 4,258,437 | 3/1981 | Sawatsky | 2/12 |

FOREIGN PATENT DOCUMENTS

| 1105438 | 6/1955 | France | 2/12 |
| 1323804 | 3/1963 | France | 2/12 |

Primary Examiner—Peter Nerbun
Attorney, Agent, or Firm—Fitch, Even, Tabin & Flannery

[57] ABSTRACT

A visor type article includes a relatively rigid arcuate shaped band member, an adjustable elastic strap cooperative with the band member in a manner to encircle the wearer's head with the band member engaging the wearer's forehead, and a replaceable visor member having a marginal edge portion adapted to be releasably inserted into a slot in an outwardly extending flange on the band member so that the visor member is supported by and extends outwardly from the band member to overlie the wearer's eyes.

7 Claims, 6 Drawing Figures

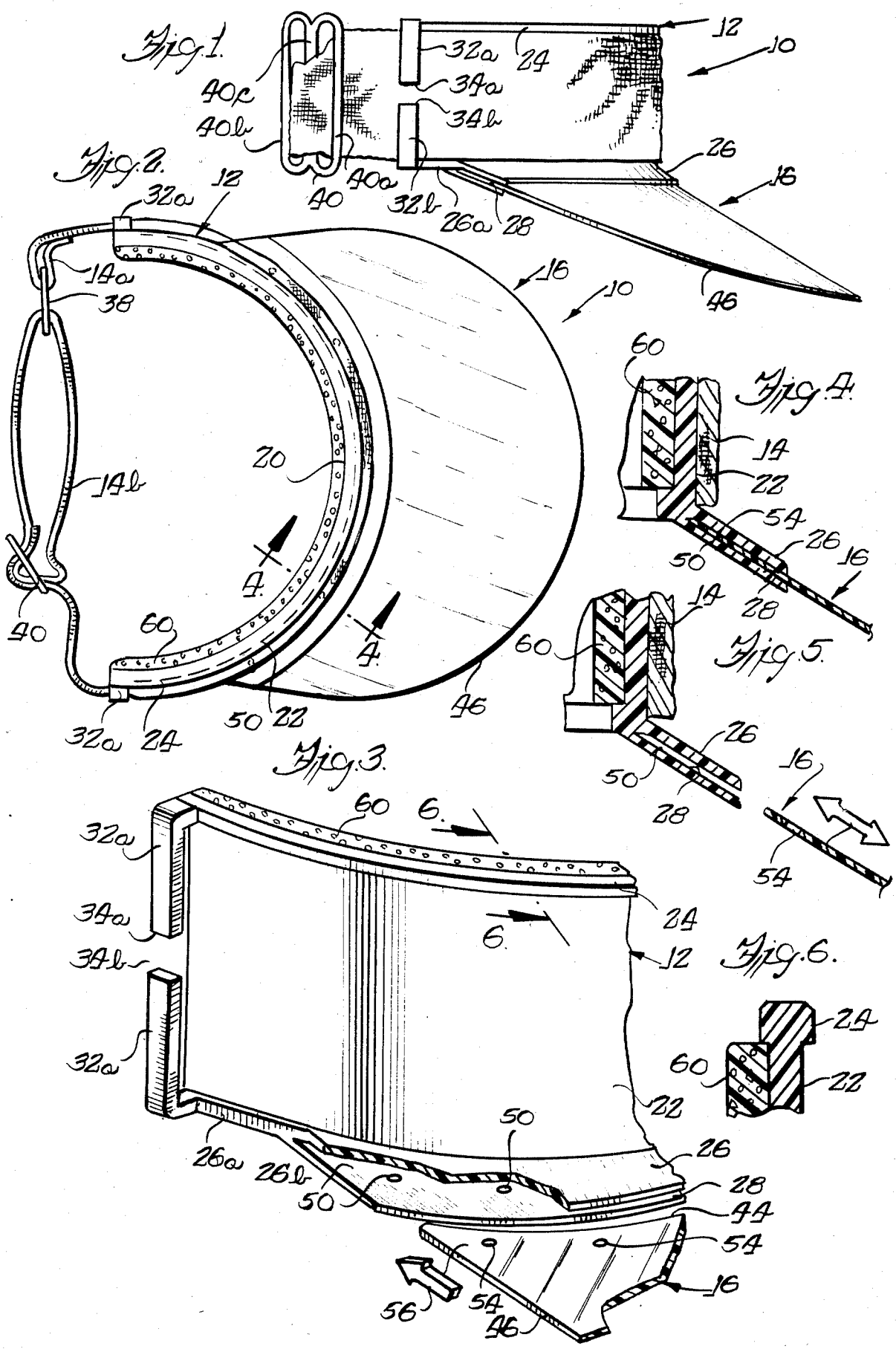

VISOR

BACKGROUND OF THE INVENTION

The present invention relates generally to visor type articles, and more particularly to a novel visor having a band member adapted for mounting on the wearer's head and on which interchangeable visor members may be releasably mounted.

Visor type articles adapted to be worn generally proximate the wearer's forehead so that an outwardly extending visor or bill member overlies and shades the upper portion of the wearer's face are generally known. Prior to the advent of florescent and indirect interior lighting, visors were frequently worn in work places to prevent glare from the more concentrated incandescent type light bulbs and thereby relieve eyestrain. For outdoor activities, visors are frequently worn to protect the eyes from the glare of the sun as well as to protect the wearer's face from the sun. In either case, it is desirable that the visor protect the wearer's eyes and/or face from the glare of the lights or sun without significantly impeding vision.

SUMMARY OF THE INVENTION

One of the primary objects of the present invention is to provide a novel visor type article which facilitates interchanging of the visor member.

A more particular object of the present invention is to provide a novel visor type article which enables interchanging of a visor or bill member by insertion into and withdrawal from a flange portion of a band member adapted to be worn generally adjacent the wearer's forehead, the visor member and flange having mutually cooperable retaining means operative to enable insertion and withdrawal of the visor member upon a simple rectilinear movement of the visor member.

A feature of the visor in accordance with the invention lies in the provision of an arcuate shaped band member adapted to engage the wearer's forehead and be releasably retained on the wearer's head by an adjustable elastic strap, the band member having an integral flange thereon in which an elongated slot is formed to releasably receive a visor or bill member through a simple rectilinear movement of the visor member into the slot.

A further feature of the visor in accordance with the invention lies in the provision of means facilitating releasable attachment of the strap to the arcuate shaped band member through edgewise lateral movement of the strap member.

Further objects and advantages of the present invention, together with the organization and manner of operation thereof, will become apparent from the following detailed description of the invention when taken in conjunction with the accompanying drawing wherein like reference numerals designate like elements throughout the several views.

BRIEF DESCRIPTION OF THE DRAWING

FIG. 1 is a side elevational view of a visor constructed in accordance with the present invention;

FIG. 2 is a plan view of the visor of FIG. 1;

FIG. 3 is a fragmentary perspective view of the visor of FIG. 1 but with the elastic strap removed and with the visor member shown during insertion into the visor member mounting flange;

FIG. 4 is a fragmentary sectional view, on an enlarged scale, taken substantially along line 4—4 of FIG. 2, looking in the direction of the arrows;

FIG. 5 is a fragmentary sectional view similar to FIG. 4 but showing the visor member removed from the associated slotted mounting flange on the band member; and FIG. 6 is a fragmentary sectional view, on an enlarged scale, taken substantially along line 6—6 of FIG. 3 and looking in the direction of the arrows.

DETAILED DESCRIPTION OF PREFERRED EMBODIMENT

Referring now to the drawing, and in particular to FIGS. 1 and 2, a visor type article constructed in accordance with the present invention is indicated generally at 10. Very generally, the visor 10 includes an arcuate shaped band member 12 on which an elastic strap 14 is releasably mounted to facilitate retention of the band member on the wearer's head. A visor or bill member 16 is releasably mounted on the arcuate shaped band member 12 so as to extend outwardly therefrom in generally downwardly inclined relation thereto. With the band member 12 engaging the wearer's forehead, the visor or bill member operates to shield the wearer's eyes from the sun or other undesirable light rays in a conventional manner.

The band member 12 may be made of a suitable plastic material having a generally semicircular arcuate configuration so as to define a rearward or inner concave surface 20 and an outer convex surface 22. An arcuate outwardly extending flange 24 is formed integral with or otherwise suitably secured to the band member 12 adjacent the upper marginal edge thereof, as viewed in FIG. 3. An outwardly extending and downwardly inclined flange 26 is formed integral with or otherwise suitably secured to the lower marginal edge of the band member 12 so as to extend about a portion of the arcuate concave surface 22, the end portions of the flange 22 terminating in reduced width marginal portions such as indicated at 26a in FIGS. 1 and 3. The downwardly inclined flange 26 has a slot or groove 28 formed therein which extends the full arcuate extent of the flange 26 and, as will be explained in greater detail hereinbelow, serves to releasably receive a marginal edge of the visor member 16.

The opposite ends of the arcuate shaped band member 12 have means formed thereon cooperative with the strap member 14 so as to releasably retain the strap member attached to the band member with the strap member extending along the outer convex surface 22 of the band member in surface contact therewith. For this purpose, each end of the band member has a pair of mutually facing retaining arms 32a and 32b which are preferably of generally L-shape and are formed integral with the band member at the upper and lower marginal flanges 24 and 26a, respectively, so that the retaining arms extend generally parallel to the outer convex surface 22 in spaced relation therefrom. The pairs of retaining arms 32a,b thus cooperate to define a recess or strap receiving slot between the retaining arms and the outer convex surface 22. The retaining arms 32a,b have end surfaces 34a,b respectively, which are spaced apart a sufficient distance to enable insertion of the strap member 14 through lateral edgewise movement of the strap member to partially insert it into one end of the slot defined by each pair of retaining arms 32a,b followed by insertion of the remaining portion of the strap into the other end of the slot through the opening or gap between the end surfaces 34a and 34b. Entry of the strap member between the retaining arms on each end of the arcuate shaped band member 12 is effected in a substantially identical manner.

The strap member 14 preferably comprises an elastic strap member made from a woven elastic material having a relatively soft texture. One end of the strap member, such as indicated at 14a in FIG. 2, is preferably looped through a slider member 38 of conventional design and secured back upon itself so as to retain the slider member 38 in fixed relation to the end of the strap member. The opposite end of the strap member 14, indicated at 14b in FIG. 2, is looped through a second slider member 40 which is substantially identical to the slider member 38 and has lateral leg portions 40a and 40b substantially parallel to an integral intermediate leg portion 40c (FIG. 1). The end 14b of the strap member 14 is preferably looped through slider member 40 and through the slider member 38 after which the end 14b is looped about the center leg 40c of the slider member 40 so as to enable selective adjustment of the circumferential length of the strap member for varying head sizes. As aforementioned, the strap member 14 when mounted on the band member 12 overlies the forward convex surface 22 of the band member. The strap member is preferably made of a width such that the upper and lower marginal edges thereof are closely adjacent the upper and lower flanges 24, 26 and 26a on the band member so that the flanges retain the strap in relatively fixed position relative to the forward band surface 22.

The visor or bill member 16 has a concave arcuate marginal edge surface 44 which, as illustrated in FIG. 3, has a radius of curvature substantially equal to the radius of curvature of the arcuate shaped band member surface 22. The arcuate marginal edge surface 44 intersects the opposite ends of a forwardly extending edge surface 46 of the visor member. The visor or bill member 16 is preferably made of a tinted plastic material having a thickness enabling the rearward edge portion thereof adjacent the arcuate edge 44 to be inserted within the slot 28 formed within the downwardly inclined arcuate flange 26 on the band member 12. In accordance with one feature of the present invention, the marginal edge portion of the visor member 16 adjacent the arcuate edge 44 and the flange 26 on the band member 12 have mutually cooperative retaining means operative to releasably retain the visor member within the slot 28, the visor member being readily removable from the slot 28 so as to enable interchanging with other similar shaped visor or bill members having different sun shield characteristics. In the illustrated embodiment, a plurality of upstanding nibs or detents 50 are formed integral with a lower portion 26b of the flange 26 so as to lie on a common circle along the length of the flange 26 in substantially equidistantly spaced relation and projecting upwardly within slot 28. Each of the nibs 50 has an upper convex cam surface formed thereon which, in the illustrated embodiment, is formed as a segmental spherical surface to enable the marginal edge 46 of the visor member to be cammed over the nibs 50 during insertion into the slot 28.

The visor or bill member 16 has a plurality of generally circular recesses or bores 54 formed therethrough which are spaced and positioned to receive a corresponding one of the nibs 50 therein when the marginal edge 44 of the visor member is inserted into the full depth of the groove 28. In this manner, the nibs 50 are cammed into the bores or recesses 54 in the rearward marginal edge of the visor or bill member to releasably retain the visor or bill member in mounted relation within the slot 28 upon rectilinear movement of the visor member in the direction of the arrow 56 shown in FIG. 3, while enabling the visor member to be readily removed therefrom by pulling on the visor in a reverse direction.

Preferably, a resilient cushion or pad 60 is affixed to the inner concave surface 20 of the band member 12, as through a suitable adhesive, so as to engage the wearer's forehead and provide a soft cushioned engagement between the forehead and the band member 12. The resilient cushion 60 may be made of any suitable resilient material such as a foam urethane having the desired cushion characteristics. The resilient cushion preferably has a width substantially equal to the width or height of the band member so as to cover substantially the full rearward exposed arcuate surface 20.

Thus, in accordance with the present invention, a visor type article is provided which may be worn on one's head and which has a resilient cushion adapted for engagement with the wearer's forehead and has an adjustable elastic strap facilitating comfortable retention on the wearer's head. A replaceable visor or bill member is carried by the band member so as to overlie the wearer's eyes and thereby shade the eyes from undesirable sun rays or other light rays, the visor member being readily interchangeable with other similar shaped visor or bill members to accommodate various light conditions.

While a preferred embodiment of the invention has been illustrated and described, it will be understood that changes and modifications may be made therein without departing from the invention in its broader aspects. Various features of the invention are defined in the following claims.

What is claimed is:

1. A visor type article having an interchangeable visor member comprising:

a generally rigid and arcuate body in the shape of a band member having a substantially semi-circular shape adapted for engagement with a wearer's forehead and having a forwardly facing arcuate surface, the band member having an outwardly extending flange portion defining an elongated slot therein;

a continuous, separable elastic strap adjustable in circumference and cooperative with the band member to encircle the wearer's head and releasably retain the band member on the wearer's head, a portion of the adjustable elastic strap extending along the forwardly facing arcuate surface of the band member, means adjacent opposite ends of the semi-circular shaped member for releasably retaining the elastic strap to the band member including portions integral with the band member spaced outwardly from the forwardly facing arcuate surface of the band member and defining a recess, the elastic strap being insertable into the recess adjacent the arcuate surface through lateral edgewise movement of the strap; means defining an arcuate slot on said band member to receive said strap therein to aid in fixing the strap to said band member, and a visor member having a marginal edge portion adapted to be inserted within the slot in the flange portion of the band member so that the visor member is supported by and extends outwardly from the band member, the flange portion and the marginal edge portion having mutually cooperative releasable retaining means engageable to releasably retain the visor member and to allow substitution of visor members by removal from and insertion into the slot.

2. A visor type article as defined in claim 1 wherein said flange portion extends substantially the full arcuate length of said band member, said slot extending the full arcuate length of said flange portion, said band member defining outwardly extending flange portions along marginal longitudinal edges thereof to retain said strap member in predetermined mounted relation thereon.

3. A visor type article having an interchangeable visor member comprising:

a generally arcuately shaped band member having a substantially semi-circular shape adapted for engagement with a wearer's forehead and having a forwardly facing arcuate surface, the band member having an outwardly extending flange portion defining an elongated slot therein;

a continuous, separable strap adjustable in circumference and cooperative with the band member to encircle the wearer's head and releasably retain the band with respect thereto, the adjustable strap being releasably received on the forwardly facing arcuate surface of the band member by a pair of mutually opposed retaining arms adjacent each end of the band member and integral therewith, each pair of mutually opposed arms having portions thereof spaced from the arcuate surface of the band member in generally parallel relation therewith and defining an opening therebetween enabling the strap to be inserted between the retaining arms and the arcuate surface through lateral edgewise movement of the strap; means defining an arcuate slot on said band member to receive said strap therein to aid in fixing the strap to said band member, and a visor member having a marginal edge portion adapted to be inserted within the slot in the flange portion of the band member so that the visor member is supported by and extends outwardly from the band member, the flange portion and the marginal edge portion having mutually cooperative retaining means including a plurality of retaining nibs defining cam surfaces thereon formed on the flange portion of the band member so as to project into the elongated slot, and the marginal edge portion of the visor member having a corresponding number of recesses formed therein adapted to releasably receive the retaining nibs when the marginal edge portion is inserted in the elongated slot, the cam surfaces on the nibs facilitating entry and release of the nibs into the recesses in the visor member.

4. A visor type article as defined in claim 3 wherein said adjustable strap is made of a length of elastic material and has its ends interconnected in a manner facilitating adjustment of the circumferential length of said strap.

5. A visor type article as defined in claim 3 including a resilient cushion member mounted on said band member for engagement with the wearer's forehead.

6. A visor type article as defined in claim 3 wherein visor member is made of a transparent material enabling visual viewing therethrough.

7. A visor type article as defined in claim 3 wherein said visor member is adapted to block sun rays from passing directly therethrough.

* * * * *